United States Patent
Suzuki

(10) Patent No.: US 6,726,821 B1
(45) Date of Patent: Apr. 27, 2004

(54) POLYACRYLAMIDE PRECAST GELS FOR ELECTROPHORESIS, PROCESS FOR PRODUCING THE SAME AND ELECTROPORESIS METHOD BY USING THE GELS

(75) Inventor: Mika Suzuki, Tokyo (JP)

(73) Assignee: Hymo Corporation, Tokyo (JP)

( * ) Notice: Subject to any disclaimer, the term of this patent is extended or adjusted under 35 U.S.C. 154(b) by 108 days.

(21) Appl. No.: 09/890,710

(22) PCT Filed: Nov. 30, 2000

(86) PCT No.: PCT/JP00/08465

§ 371 (c)(1),
(2), (4) Date: Aug. 2, 2001

(87) PCT Pub. No.: WO01/40789

PCT Pub. Date: Jun. 7, 2001

(30) Foreign Application Priority Data

Dec. 2, 1999 (JP) .............................. 11-343835
Feb. 29, 2000 (JP) ........................ 2000-054166
Mar. 2, 2000 (JP) ........................ 2000-057478

(51) Int. Cl.[7] ....................... G01N 27/26; G01N 27/447
(52) U.S. Cl. ....................... 204/456; 204/468; 204/469; 204/606
(58) Field of Search ................. 204/468, 469, 204/470, 456, 606

(56) References Cited

U.S. PATENT DOCUMENTS 4,522,742 A * 6/1985 Lee et al. ............... 252/301.16

FOREIGN PATENT DOCUMENTS

| EP | 0 566 784 A1 | * | 10/1993 |
| JP | 4-184163 A | | 7/1992 |
| JP | 9-512907 A | | 12/1997 |
| WO | WO 96/16724 A1 | | 6/1996 |
| WO | WO 97/04315 A1 | | 2/1997 |

* cited by examiner

Primary Examiner—Kaj K. Olsen
(74) Attorney, Agent, or Firm—Browdy and Neimark, P.L.L.C.

(57) ABSTRACT

A precast acrylamide electrophoresis gel is disclosed, which includes a gel buffer solution containing either Tris and glycine or Tris, glycine and any one or more than two of ampholytes, and a monobasic acid, titrated to a specified pH range. With the gels constituted as stated earlier, proteins can be successfully subjected to electrophoresis using the commonly available Laemmli's buffer system, while the DNA can be also satisfactorily run on the gel using the electrophoresis electrode solution containing Tris, chelating agent, and any one acid of acetic acid, phosphoric acid and boric acid. In either of protein and DNA analyses, the gels even after stored under refrigeration more than six months are fully comparable in resolution and clearness of electrophoretic pattern to the gels just after being prepared. Where the DAN is subjected to electrophoresis using either the Laemmli's buffer or the Ornstein and Davis buffer, commonly used in electrophoresis of proteins, the gels even after storage under refrigeration over four months may exhibit the electrophoretic patterns comparable in resolution and clearness to the gels soon after being produced.

10 Claims, No Drawings

POLYACRYLAMIDE PRECAST GELS FOR ELECTROPHORESIS, PROCESS FOR PRODUCING THE SAME AND ELECTROPORESIS METHOD BY USING THE GELS

REFERENCE TO RELATED APPLICATIONS

The present application is the national stage under 35, U.S.C. 371, of international application PCT/JP00/08465, filed Nov. 30, 2000, which designated the United States, and which international application was not published under PCT Article 21(2) in the English language.

TECHNICAL FIELD

The present invention relates to a precast polyacrylamide gel adapted for use in electrophoresis separation, production method thereof and electrophoresis using the gel.

BACKGROUND ART

Precast polyacrylamide gels for electrophoresis are extensively used as a basic investigative medium for detecting and quantitatively analyzing chemical substances: proteins, nucleic acids, carbohydrates, and lipids necessary for building all living organisms in fields as diverse as biology, medicine, fisheries, veterinary medicine, and so on. Especially, a variety of precast polyacrylamide gels different in resolving power can be made easily by varying a gel recipe because the gels are substances synthesized artificially. Accordingly, it is possible to prepare in advance the precast gels differing diversely in separation characteristic or resolution from one another. The artificial gels, since much saving the labor and effort for analytic procedure and excellent in uniformity and reproducibility, have helped the productivity and quality control in the fields stated earlier. The artificial gels which are mass-produced must have an increased shelf-life to ensure an adequate supply of these gels.

Most polyacrylamide gels for electrophoresis used extensively for analytic technique of proteins in the fields of biochemistry and medicine are based on the system developed by Ornstein [L. Ornstein, Ann. N.Y. Acad. Sci. 121, 321–349, (1964)] and Davis [B. J. Davis, Ann. N.Y. Acad. Sci. 121, 404–427(1964)] or that proposed by Laemmli [U. K. Laemmli, Nature, 227, 680 (1970)]. Gels have heretofore been produced by the users or analysts in themselves or on themselves for their private use. In particular, the Laemmli system is most extensively used, since the molecular weights of proteins can be simply presumed by adding sodium dodecyl sulfate, contracted to "SDS" hereinafter, to gels or electrophoresis buffer solutions. The Laemmli system consists of a gel buffer solution of tris(hydroxymethyl) aminomethane, contracted to "Tris" herein, which is partially neutralized with hydrochloric acid, and an electrophoresis buffer solution, or Laemmli's electrophoresis buffer solution using Tris and glycine salt. The gel buffer solution in the system stated earlier, or Laemmli's gel buffer solution contains about 10–20 mol % Tris partially neutralized to be adjusted to pH 8.8 with hydrochloric acid. At this pH of the Laemmli's gel buffer solution, however, amide groups are subjected to hydrolysis time elapses. As the hydrolysis of gels proceeds even under low temperatures, the polyacrylamide gels come to contain partially anionic groups. As a result, the migration distances of proteins are reduced while electrophoretic patterns become vague, and therefore it is impossible to preserve the gels over a prolonged period.

The following discussions will present the electrophoresis of nucleic acids. Recently remarkable development of molecular biology has come to need the analysis and preparation of deoxyribonucleic acid (DNA) and ribonucleic acid (RNA). The analysis of nucleic acids mostly depends on either the agarose electrophoresis separation process or the precast polyacrylamide gel electrophoresis separation process. As nucleic acids present strong negative charges in the neutral buffer solution while the mobility thereof depends on the molecular sieve effect of supportive matrix gels, either an about 0.3–2% agarose gel or an about 3.5–20% polyacrylamide gel is chiefly employed depending on the size of nucleic acids undergoing analysis.

The agarose gel, because of having a larger pore size, is often used for analytic separation of macromolecular nucleic acids. There are many types of agarose gels, which differ from one another in electroosmosis, gel strength, melting point, and so on. Moreover, because the agarose gels are naturally occurring materials, the differences in quality are frequently seen., even for a lot of products and even for the same gels produced in the same facility. For purifying DNA by virtue of the agarose gel electrophoresis separation process, any other purification procedures such as the phenol extract, and so on must be considered because contamination with impurities in the agarose gels would inhibit enzyme activities of restriction enzymes, DNA polymerases, DNA synthetase, and so on.

In contrast, polyacrylamide gels with relatively small pore size are useful for isolation and analysis of nucleic acids of medium and/or low molecular weight. Because the polyacrylamide gels are artificially synthetic products, they are very pure chemically, and thus involving no major problems seen in the agarose gels. Moreover, the polyacrylamide gels may be easily prepared in diverse types of gels, which are different in separation characteristics, depending on the desired gel recipe. Accordingly, it is possible to prepare in advance the precast gels differing diversely in separation characteristics from one another. The use of artificial gels mass-produced in advance diverse separation characteristics, since much saving the labor and effort for analytic procedure and excellent in uniformity and reproducibility, will help productivity and quality control in the fields stated earlier. The artificial gels obtained by mass-production methods have increased shelf-life because of preservation. The most common buffer system for using agarose and polyacrylamide as the gel material in the electrophoresis separation of DNA is a continuous buffer system of around pH 7.8 to 8.3, in which a gel buffer solution is equal in composition with an electrophoresis buffer solution: a tris-acetic acid buffer, contracted to "TAE" herein, which contains either ethylenediaminetetraacetic acid, contracted to "EDTA" or disodium ethylenediaminetetraacetate, contracted to "ETA"; a tris-boric acid buffer, abbreviated to "TBE"; and a tris-phosphoric acid, abbreviated to "TPE".

As stated earlier, the precast gels manufactured on mass-production methods must be able to maintain the long-lasting shelf-life in preservation throughout shipping and storage. Among the prior processes for manufacturing gels which are superior in shelf-life is a process for manufacturing a polyacrylamide gel having the increased shelf-life disclosed in Published Unexamined Patent Application in Japan No. H04-184 163, which involves a gel buffer solution composed of Tris, ampholyte and acid to be storable for a prolonged period without loss of performance and also expanded remarkably in molecular weight range applicable for analytical electrophoresis. The polyacrylamide electrophoresis gel produced by the process recited just above is available for analysis using Laemmli's electrophoresis buffer solution. The polyacrylamide gel contains the ampholyte and has the pH of ranging from 4.0 to 7.5. In an example disclosed, the gel having a pH of ranging from 6.9 to 7.4 is produced, which is described to be stored under refrigeration for four months without variation in mobility of proteins.

The gel buffer solution is set high in neutralization rate of tris to depress the hydrolysis of the polyacrylamide gel, while added with the ampholyte to make gentle a variation in electric potential gradient neighboring a boundary between tris strong acid salt part and tris week acid salt part, thereby coming to exhibit the wide range in the fractionated molecular weight of species undergoing measurement, which is comparable to the gels fabricated using the Laemmli's electrophoresis buffer solution.

Nevertheless, most polyacrylamide gels containing a gel buffer solution of the pH range 6.9 to 7.4 begin to vary in electrophoretic mobility of proteins after more than five months in storage under refrigeration has gone by. Moreover, the polyacrylamide gel in the form of slab gel is apt to change in shape of gel, tending to dislocate the glass plates. This results in major problems of rendering handling procedure on the electrophoretic analysis worse, causing the cracking of the gels due to the dislocation of the glass plates, and so on. Although it will be speculated that the gels may be improved in shelf life with a gel buffer solution of pH 6.8 or less, such gels have disadvantages of being time-consuming for electrophoretic migration and also reducing in the resolution. Thus, none could not have succeed in developing a polyacrylamide gel that can be stored for over five months without loss of performance, superior in the resolution for proteins, and also exhibit the wide range in the fractionated molecular weight of species undergoing measurement, which is comparable to the gels fabricated using the Laemmli's gel buffer solution.

In addition, International Publication Number WO 95/27 197 discloses a buffer system for a long-lasting precast electrophoresis gel wherein separation occurs at neutral pH. The gel buffer solution in the buffer system contains a mono organic amine or substituted amine with a pH near neutrality, titrated with hydrochloric acid to a pH of between about pH 6 and about pH 7. The electrophoresis buffer solution in the buffer system recited above contains a zwitterion selected from the group of MOPS, MES, ACES, MOPSO, TES, HEPES and TAPSO, titrated to a pH of about pH 7 with sodium hydroxide or organic base. Both the gel buffer solution and the electrophoresis buffer solution are kept at neutral pH and in doing so the polyacrylamide gel itself is less subject to hydrolysis while proteins are separated with remaining completely reduced. The electrophoresis gel system recited earlier is described to have an increased useful shelf-life up to twelve months.

Nevertheless, the buffer system disclosed in International Publication Number WO 95/27 197 requires using special molecule markers, or molecules of known molecular weights. Moreover, the polyacrylamide in International Publication Number WO 95/27 197 gets slower in the rate of electrophoretic migration when using any prior electrophoresis buffer solution, for example a commonly available Laemmli's electrophoresis buffer solution containing glycine. Thus, it is impossible to use polyacrylamide for analytic separation of proteins.

The polyacrylamide controlled to a pH ranging from neutral to acid, which is considerably resistant to hydrolysis, may serve well as the electrophoresis gel improved in shelf life. That is, the polyacrylamide set at a pH ranging from neutral to acid is prolonged in shelf life, and thus may be produced in advance by mass production methods to have diverse separation characteristics. If the polyacrylamide gel combined with the precast gel technology makes it possible to separate analytically DNA by the use of the electrophoresis buffer solution available for the electrophoresis of proteins, and also to separate analytically DNA by the use of the electrophoresis buffer solution commonly available for the electrophoresis of nucleic acids, it will be expected to realize the electrophoretic analysis with efficiency at low costs.

DISCLOSURE OF THE INVENTION

A primary object of the present invention to solve the subject matter stated earlier is to provide a precast polyacrylamide gel that can be stored under refrigeration over more than six months with preserving the gel shape without loss of resolution of proteins, while coming to exhibit the wide range in the fractionated molecular weight of species undergoing measurement, which is comparable to the gels fabricated using the Laemmli's electrophoresis buffer solution.

A second object of the present invention to solve the subject matter stared earlier is to provide an electrophoresis method of separating and analyzing distinctly DNA by the use of a polyacrylamide electrophoresis gel storable under refrigeration over more than six months without loss of performance, together with an electrophoresis buffer solution availed commonly for the analytic separation of nucleic acids.

A third object of the present invention to solve the subject matter stated earlier is to provide an electrophoresis method of separating and analyzing distinctly DNA by the use of a polyacrylamide gel available for separation of proteins and storable under refrigeration over more than four months without loss of performance, together with an electrophoresis buffer solution for the analysis of proteins.

In an aspect of the present invention, a precast polyacrylamide gel adapted for use in gel electrophoresis is disclosed, in which an electrophoresis buffer solution is composed of an aqueous solution containing a tris (hydroxymethyl) aminomethane and an ampholyte, and wherein the tris(hydroxymethyl) aminomethane is present in a concentration of between 0.07 mol/litre and 0.2 mol/litre while the ampholyte is composed of glycine and at least one conjugate ampholyte, which has a basic dissociation constant of 8.3 pKb 9.6, the conjugate ampholyte added ranging in amount from 0.1 to 30 mol % with respect to the glycine, concentrations of the conjugate ampholyte and the glycine ranging in all between 0.1 and 0.3 mol/litre, and a pH range being between pH 6.0 and pH 6.8.

The precast polyacrylamide gel of the present invention can be stored under refrigeration for over six months without loss of resolution and gel configuration, and also exhibit the wide range in the fractionated molecular weight of species undergoing measurement, which is comparable to the gels fabricated using the Laemmli's electrophoresis buffer solution.

In another aspect of the present invention, there is disclosed that the conjugate ampholyte is an amino acid having the same number of anionic and cationic groups in a molecule.

In a further another aspect the present invention, there is disclosed that the conjugate ampholyte is at least one selected from serine, glutamine, tryptophan, methionine and phenylalanine.

In another aspect of the present invention, a process for fabricating a precast polyacrylamide gel suitable for electrophoresis is disclosed, which is comprised of polymerizing an admixture of an acrylamide, polyfunctional crosslinking agent, water and a buffer solution of composition defined in the following (1) and (2) in the presence of a polymerization initiator under the condition of pH range 6.0 6.8:

(1) a tris(hydroxymethyl) aminomethane is present in a concentration of between 0.07 mol/litre and 0.1 mol/litre; and (2) an ampholyte is composed of glycine and at least one conjugate ampholyte,
  (a) the conjugate ampholyte has a basic dissociation constant of 8.3 pKb 9.6,
  (b) the conjugate ampholyte added ranges in amount from 0.1 to 30 mol % with respect to the glycine, and
  (c) a total concentration of the conjugate ampholyte and the glycine ranges between 0.1 and 0.3 mol/litre.

According to the process for fabricating a precast polyacrylamide electrophoresis gel as stated earlier, the improved precast polyacrylamide electrophoresis gel may be obtained with efficiency, which is increased in the useful shelf life where the gel can be stored for over six months without loss of resolution and gel configuration.

In another aspect of the present invention, a use of the precast polyacrylamide electrophoresis gel is disclosed, in which the analytic separation of proteins is performed using the electrophoresis buffer solution containing glycine and tris(hydroxymethyl) aminomethane with added dodecyl sulfate.

The use of the precast polyacrylamide electrophoresis gel as stated just above makes it possible to realize the wide range in the fractionated molecular weight of species undergoing measurement, which is comparable to the gels fabricated using the Laemmli's gel electrophoresis buffer solution.

In a further another aspect of the present invention, an electrophoresis system for DNA is disclosed, which makes use of an electrophoresis buffer solution containing tris (hydroxymethyl) aminomethane and a precast polyacrylamide gel characterized by the following (1) and (2);

(1) a gel buffer solution contained in the precast polyacrylamide gel contains tris(hydroxymethyl) aminomethane, at least one ampholyte rendering glycine indispensable, and a monobasic acid, titrated to a pH of between pH 6.0 and pH 7.5, and (2) the ampholyte contained in the gel buffer solution has a basic dissociation constant of 8.3 pKb 9.6, and includes an amino acid having the same number of anionic and cationic groups in a molecule.

In another aspect of the present invention, the gel buffer solution contains a monobasic acid consisting of at least one of hydrochloric acid and acetic acid, titrated to a pH of between pH 6.0 and pH 6.5 to increase the useful shelf life of a precast gel.

In another aspect of the present invention, the gel buffer solution contains a monobasic acid consisting of at least one of hydrochloric acid and acetic acid, titrated to a pH of between pH 6.5 and pH 7.5 to increase the useful shelf life of a precast gel.

In another aspect of the present invention, an electrophoresis buffer solution is disclosed which contains, aside from tris(hydroxymethyl) aminomethane, components defined in the following (1) and (2), titrated to a pH in a pH range 7.8 8.3:

(1) any one of acetic acid, phosphoric acid and boric acid; and (2) a chelating agent of disodium ethylenediaminetetraacetate.

In a further another aspect of the present invention, there is disclosed the electrophoresis buffer solution containing the monobasic acid of boric acid.

In another aspect of the present invention, there is disclosed the electrophoresis buffer solution containing an ampholyte, aside from tris(hydroxymethyl) aminomethane, and titrated to a pH in a pH range 7.8 8.3.

In another aspect of the present invention, there is disclosed the electrophoresis buffer solution containing the ampholyte of glycine.

In a further another aspect of the present invention, there is disclosed the electrophoresis buffer solution containing dodecyl sulfate, in addition to the ampholyte of glycine.

BEST MODE FOR CARRYING OUT THE INVENTION

In accordance with the present invention, a gel adapted for use in analytic separation of proteins is provided, which is enhanced in the useful shelf-life thereof. The gel contains therein a buffer solution composed of Tris, glycine and at least one conjugate ampholyte, the Tris ranging in concentration in the gel from 0.07 mol/litre to 0.2 mol/litre, preferably from 0.08 mol/litre to 0.2 mol/litre. The limited concentration range recited above results in inclusion of leading ions enough in amount to ensure the electrophoresis time comparable to the gels fabricated using the Laemmli's gel buffer solution. With the Tris less in concentration in the gel than 0.07 mpl/litre, the electrophoretic pattern becomes overall too vague to avail for the analytic separation of proteins. In contrast, even if the concentration of the Tris in the gel is over 0.2 mol/litre, the concentration of the leading ion in the gel becomes too high, thereby prolonging the electrophoresis time, making the operational efficiency of the analysis worse.

The ampholyte is composed of glycine and at least one conjugate ampholyte that has the basic dissociation constant of 8.3 pKb 9.6, preferably 9.0 pKb 9.6. Only glycine by itself, especially when the gel buffer solution is at pH 7 or less, can not realize the wide range in the fractionated molecular weight of species undergoing measurement, which is comparable to the gels fabricated using the Laemmli's gel buffer solution. On the other hand, with the conjugate ampholyte of pKb 8.3, the ampholyte is lower in pKb than the Tris, and for the sake of which the gel buffer solution is varied in pH to make the fractionated molecular weight range much broaden. In contrast, if the conjugate ampholyte is in the condition of pKb 9.6, the ampholyte exceeds the glycine in basic dissociation constant, making no contribution to helping ensure the gentle potential gradient. To cope with this, when the conjugate ampholyte is selected from the group of serine, tryptophan, phenylalanine, and so on satisfying 9.0 pKb 9.6, the ampholytes migrate consecutively towards the anode side to their respective positions on the basis of the pKb value, with the smallest pKb migrating to the position most neighboring the anode, so that the gentle potential gradient may be established in the gel. Thus, the precast polyacrylamide gel of the present invention succeeds in realizing the wide range in the fractionated molecular weight of species undergoing measurement, which is comparable to the gels fabricated using the Laemmli's gel buffer solution.

According to the present invention, the amount of the conjugate ampholytes added is from 0.1 to 30 mol %, preferably from 1 to 20 mol %, with respect to glycine. When the conjugate ampholyte added is less in amount than 0.1 mol %, the precast polyacrylamide gel fails in realizing the wide range in the fractionated molecular weight of species undergoing measurement, which is comparable to the gels fabricated using the Laemmli's gel buffer solution. To the contrary, if the conjugate ampholyte is added over 30 mol %, the electrophoretic image appearing on the gel becomes too vague to have any practical use.

The total concentration of the conjugate ampholyte and glycine is in the range of from 0.1 mol/litre to 0.3 mol/litre, preferably from 0.1 to 0.2 mol/litre. Even when the ampholyte is either less than 0.1 mol/litre or more than 0.3 mol/litre, the electrophoretic pattern on the gel also becomes vague to be unavailable for practical use thereof.

The ampholytes used in the present invention preferably have the same number of anionic and cationic groups in a molecule. All the anionic and cationic groups dissociate into ions in the gel buffer solution so that the ampholytes become electrically neutral. At a pH higher than pKb, only the anionic groups dissociate while the cationic groups are less subject to the dissociation so that the ampholytes is charged negatively. Thus, it will be understood that the ampholytes behave substantially like weak monobasic acid.

The given pH of the gel buffer solution for the precast polyacrylamide gel of the present invention, the use and production thereof is adjusted to from 6.0 to 6.8, preferably to 6.3. When the buffer solution is above pH 6.8, the polyacrylamide is susceptible to hydrolysis, and thus can not be stored for a long period without loss of performance. In contrast, if the gel buffer solution is less than 6.0 in pH, the polyacrylamide gel may keep the increased shelf-life while the electrophoretic patterns of proteins are liable to become too vague to have the practical use. The polyacrylamide gel with the gel buffer solution adjusted to pH 6.8 can be stored under refrigeration over six months with no loss of performance. When controlled to just pH 6.3, the gels obtained are remarkably retarded in the rate of hydrolysis compared with the pH 6.8, because the pH 6.3 is near to the pH of the acrylamide itself. This makes it possible to store the gels for over a year with no change or deterioration in gel shape and electrophoretic pattern due to acrylamide hydrolysis.

The use of the precast polyacrylamide gels according to the present invention is an analytic separation of proteins, which employs the electrophoresis buffer solution containing Tris and glycine, preferably containing Tris of 0.025 mol/litre, glycine of 0.192 mol/litre and SDS of 0.1% by weight. The electrophoresis buffer solution, because of having the same composition found in the extensively used Laemmli's gel buffer solution, serves well for the analytic separation of proteins with inexpensive cost and efficiency. Selection of an ampholyte, for example MOPS rather than glycine for the electrophoresis buffer solution may also serve for the analytic separation of proteins. Nevertheless, the fractionated molecular weight range performed by the gel is broader, compared with the gel fabricated using the Laemmli's gel buffer solution used extensively.

The precast polyacrylamide gel of the present invention may be produced in the same fashion as the production of the prior polyacrylamide electrophoresis gels, excepting pH regulation and addition of ampholytes. For instance, N,N'-methylene bis-acrylamide, contracted to "BIS" herein, is among the most extensively used water-soluble divinyl compounds, which are able to conjugate with the acrylamide for cross-linking the acrylamide. Any other suitable cross-linker may be utilized such as N,N'-diallyltartardiamide, which is a kind of the commonly available water-soluble divinyl compounds.

An aqueous monomer solution used in the precast polyacrylamide gel of the present invention may include a water-soluble polymer such as agarose, polyacrylamide, polyvinyl alcohol, polyvinyl pyrollidone, polyethylene oxide, polymethyl vinylether, and so on to endow the gel with elasticity and increase the gel strength. Alternatively, the monomer solution may be copolymerized with other monomers.

Copolymerization of monomers in the production of the precast polyacrylamide gel of the present invention takes place with radicals resulting from either polymerization initiator or exposure to any of ultraviolet light and ionizing radiation. The polymerization initiator is preferably, but limited to a polymerization initiator of redox system in which a peroxide such as ammonium persulfate, and so on is simultaneously used with a reducing agent such as N,N, N',N'-tetramethylethylenediamine, contracted to TEMED herein, and so on. The peroxide and reducing agent are used in the range of from 0.05 to 5% by weight/volume based on the total monomer. Copolymerization temperature, although unspecified as long as the initiator is allowed to serve well, is preferably in the range of from 15 to 50.

The following description will present the electrophoresis separation for DNA in which the precast polyacrylamide gel constructed according to the present invention to have the increased shelf-life is used in combination with the electrophoresis buffer buffer solution commonly used for the analytic separation of nucleic acid.

The gel buffer solution contains Tris, any one or more ampholytes including glycine, and a monobasic acid. Preferably, the gel buffer solution contains Tris, glycine, an amino acid having the same number of anionic and cationic groups in a molecule of 8.3 pKb 9.6 in basic dissociation constant, hydrochloric acid and acetic acid. The gel buffer solution without any one or more than two of ampholytes including glycine, when made acidic in pH, gets Tris to rise in neutralization rate, causing much more variation in the potential gradient at an area neighboring a boundary between the tris strong acid salt part and the tris week acid salt part. This is apt to incur focusing of separated molecules near the boundary area, rendering the fractionated molecular weight range much reduced. Besides, the electrophoresis time is prolonged so that the separation operation is intolerably retarded in efficiency.

Since glycine may serve well to make gentle the change in potential gradient at the area near the boundary between the tris strong acid salt part and the tris week acid salt part in the electrophoresis gel, it is inevitable for realizing the wide range in the fractionated molecular weight of species undergoing measurement, which is comparable to the gels fabricated using either the TBE or the Ornstein and Davis gel buffer solution. Nevertheless, even if the gel buffer solution is made much acid in pH, glycine can not control the change in potential gradient alone. To cope with this, it is desired in the gel buffer solution to conjugate glycine with any amino acid having the same number of anionic and cationic groups in a molecule of 8.3 pKb 9.6 in basic dissociation constant. This makes it possible to render the potential gradient in the electrophoresis gel gentle.

The amino acids conjugated with glycine have the basic dissociation constant pKb of 8.3 pKb 9.6, more preferably of 9.0 pKb 9.6. In case where the amino acids conjugated with glycine has pKb 8.3, the amino acids are lower in pKb than the Tris, and for the sake of which the gel buffer solution is varied in pH to make the fractionated molecular weight range much broadening. Conversely, when glycine is conjugated with the amino acids of pKb 9.6, the amino acids exceed the glycine in pKb, making no contribution to helping ensure the gentle potential gradient. Where the amino acids of 9.0 pKb 9.6 are used in the gel buffer solution, they migrate consecutively towards the anode side to their respective positions on the basis of the pKb value, with the smallest pKb migrating to the position most neighboring the anode, so that the gentle potential gradient may be established in the gel. Among the amino acids satisfying 9.0 pKb 9.6 are serine, tryptophan, phenylalanine, and so on. According to the present invention, serine is preferred.

Moreover, it is desirable that the amino acids conjugated with glycine have the same number of anionic and cationic groups in a molecule. At a pH somewhat lower than pKb, all the anionic and cationic groups dissociate completely into ions so that the amino acids takes on electric neutrality. In contrast, at a pH higher than pKb, only the anionic groups dissociate whereas the cationic groups are retarded in dissociation, so that the amino acids are charged negatively. Thus, the amino acids exhibit substantially the behavior as monobasic weak acid to be allowed to use them as quasi-weak acid. Previously adding any quasi-weak acid to the gel buffer solution results in lowering an electric resistance of the tris-weak acid salt part in the electrophoresis gel. Under the presence of strong acid radicals, in addition, the pH is so low that the amino acids become electrically neutral, thus making no contribution to electric conduction.

The pH of the gel buffer solution is in the range of from 6.0 to 7.5, preferably from 6.0 to 6.5. With the pH above 7.5, the polyacrylamide gels, because of being subjected to hydrolysis over time, are limited in shelf-life thereof. Conversely, the pH below 6.0, although increasing the useful shelf-life of the polyacrylamide gels, raises the neutralization rate of Tris to an extent that might impair the effects of the buffer system. In order to increase the useful shelf-life of the precast polyacrylamide gels, it is preferable to get the pH of the gel buffer solution to near the pH of the acrylamide per se.

On the other hand, the electrophoresis buffer solution contains Tris, chelating agent, and any one acid of acetic acid, phosphoric acid and boric acid, preferably boric acid. With the gel buffer solution adjusted to a pH in the pH range of from 6.0 to 6.5, the Ornstein and Davis electrophoresis buffer solution is not practical for the analytic separation of DNA because the electrophoretic patterns obtained become vague. The TBA employed in the present invention contains Tris of 0.0892 mol/litre, boric acid of 0.0890 mol/litre and ETA of 0.0025 mol/litre, preferably titrated to pH 8.3. The buffer system of the composition stated just earlier is the TBE extensively used for analytic separation of nucleic acid, and therefore may serve well for the analysis with inexpensive cost and efficiency. Moreover, the buffer system stated earlier makes it possible to finish the electrophoresis within a limited short period of time while ensuring very clear patterns. Either of TAE and TPE, although enabling the analytic separation of DNA, needs plenty of time to conduct the electrophoresis while becoming worse in the analytic efficiency, compared with the TBE.

The following description will present the electrophoresis separation for DNA in which the precast polyacrylamide gel constructed according to the present invention to increase in the useful shelf-life is used in combination with the electrophoresis buffer solution commonly used for the electrophoresis of proteins.

The gel buffer solution contains Tris, any one or more than two of ampholytes including glycine, and a monobasic acid. Preferably, the gel buffer solution contains Tris, glycine, an amino acid having the same number of anionic and cationic groups in a molecule of 8.3 pKb 9.6 in basic dissociation constant, hydrochloric acid and acetic acid. The gel buffer solution without any one or more than two of ampholytes including glycine, when made acidic in pH, gets Tris to rise in neutralization rate, causing much more variation in the potential gradient at an area neighboring a boundary between the tris strong acid salt part and the tris weak acid salt part. This is apt to incur focusing of separated molecules undergoing analysis nearby the boundary area, rendering the fractionated molecular weight range much reduced. Besides, the electrophoresis time is prolonged so that the separation operation is intolerably retarded in efficiency.

Since glycine may serve well to make gentle the change in potential gradient at the area near the boundary between the tris strong acid salt part and the tris weak acid salt part even in the low pH gel buffer solution, the existence of glycine in the gel buffer solution is inevitable for realizing the wide range in the fractionated molecular weight of species undergoing measurement, which is comparable to the gels fabricated using either the TBE or the Ornstein and Davis gel buffer solution. Nevertheless, when the gel buffer solution is made more acid in pH, glycine can not control the change in potential gradient alone. To cope with this, it is desired in the gel buffer solution to conjugate glycine with any amino acid having the same number of anionic and cationic groups in a molecule of 8.3 pKb 9.6 in basic dissociation constant. This makes it possible to render the potential gradient in the electrophoresis gel gentle.

The amino acids to be conjugated with glycine have the basic dissociation constant pKb of 8.3 pKb 9.6, more preferably of 9.0 pKb 9.6. In case where the amino acids conjugated with glycine has pKb 8.3, the amino acids are lower in pKb than the Tris, and for the sake of which the gel buffer solution is varied in pH to make the fractionated molecular weight range much broadening. Conversely, when glycine is conjugated with the amino acids of pKb 9.6, the amino acids exceed the glycine in pKb, making no contribution to helping ensure the gentle potential gradient. Where the amino acids of 9.0 pKb 9.6 are used in the gel buffer solution, they migrate consecutively towards the anode side to their respective positions on the basis of the pKb value, with the smallest pKb migrating to the position most neighboring the anode, so that the gentle potential gradient may be established in the gel. Among the amino acids satisfying 9.0 pKb 9.6 are serine, tryptophan, phenylalanine, and so on. According to the present invention, serine is preferred.

Moreover, it is desirable that the amino acids conjugated with glycine have the same number of anionic and cationic groups in a molecule. At the pH somewhat lower than pKb, all the anionic and cationic groups dissociate completely into ions so that the amino acids takes on electric neutrality. In contrast, at the pH higher than pKb, only the anionic groups dissociate whereas the cationic groups are retarded in dissociation, so that the amino acids are charged negatively. Thus, the amino acids exhibit substantially the behavior as monobasic weak acid to be allowed to use them as quasi-weak acid. Previously adding any quasi-weak acid to the gel buffer solution results in lowering an electric resistance of the tris-weak acid salt part in the electrophoresis gel. Under the presence of strong acid radicals, in addition, the pH is so low that the amino acids become electrically neutral, thus making no contribution to electric conduction.

The pH of the gel buffer solution is in the range of from 6.5 to 7.5, preferably from 6.5 to 7.0. With the pH above 7.5, the polyacrylamide gels, because of hydrolysis over time, are limited in shelf-life thereof. Conversely, a pH below 6.5, although increasing the useful shelf-life of the polyacrylamide gels, results in unsatisfactory electrophoresis patterns.

The electrophoresis buffer solution employable in the present invention is the Ornstein and Davis electrophoresis buffer solution containing 0.025 mol/litre Tris and 0.192 mol/litre glycine, titrated to the pH 8.3. The buffer solution composed as stated earlier is the electrophoresis buffer solution extensively used in the analytic separation of proteins and, therefore, may serve well with good efficiency to obtain very clear electrophoresis results.

For the electrophoresis buffer solution of the present invention, alternatively, the Laemmli's electrophoresis buffer solution commonly used in the protein analyses may be also adopted, which contains 0.025 mol/litre Tris, 0.192 mol/litre glycine and 0.1%(w/v) SDS. Thus, both the analytic separations of DNA and proteins may be run on the same electrophoresis buffer solution. This contributes to the efficient operation and cost reduction.

While the present invention will be explained with reference to the following examples, it should be understood that such examples are not restrictive, but are for illustrative purposes only.

EXAMPLE 1

Arranged between a rectangular glass sheet of 12 cm in width and 10 cm long and another glass sheet of the same dimension made at an upper end thereof with a recess were a spacer of 1 mm in thickness and a silicon seal to keep monomer solution from leaking. They were assembled into a glass plate cell. Monomer solutions were prepared, each of which was composed of a 10% acrylamide (%T: "total monomer concentration in the solution"), a 5% Bis (%C: "concentration of Bis"), and any one of buffer solutions composed as shown in Table 1 below. The monomer solutions were added and blended with 0.0025 mol/litre APS and 0.0075 mol/litre TEMED. The resultant mixture was poured into the glass plate cell where polymerization was allowed at 25 to yield a polyacrylamide gel for electrophoresis.

The protein marker, or commercially available protein of known molecular weight, was electrophoresed on the polyacrylamide electrophoresis gel obtained as stated earlier to measure the migration distance. The protein marker was first treated with 2-mercaptoethanol and SDS and further added with a 0.5wt % bromphenol blue, contracted to BPB herein, and 7wt % grease to be used for a test. The electrophoresis buffer solution had the composition of Laemmli system composed of 0.025 mol/litre Tris, 0.192 mol/litre glycine, 0.1 wt % SDS. The electrophoresis was done using a constant current of 20 millamps. Electric conduction was halted just when the electrophoretic end of BPB had reached 5 mm above the bottom of the gel. The staining was carried out using 0.25 vol % Coomassie Brilliant Blue, contracted to CBB hereinafter, G-250, 10 vol % acetic acid, and 30 vol % methanol solution with shaking for 45 min. while the destaining was performed using 7 vol % acetic acid, 3 vol % methanol solution with shaking for 90 min. Table 2 shows the mobility just after being produced while Table 3 is the mobility after stored at 5 for six months. The mobility is defined as the migration distance of protein in percent: (Mobility %)=(Distance of each band from the lower end of well) (Distance of the electrophoretic front of BPB from the lower end of well) 100

TABLE 1

Compositions of gel buffer solutions

| | Sample-1 | Sample-2 | Comp.-1 | Comp.-2 | Comp.-3 |
|---|---|---|---|---|---|
| Tris (mol/litre) | 0.082 | 0.08 | 0.375 | 0.075 | 0.082 |
| Glycine (mol/litre) | 0.167 | 0.162 | — | 0.192 | 0.182 |
| Serine (mol/litre) | 0.025 | 0.03 | — | — | — |
| Tricine (mol/litre) | — | — | — | — | 0.01 |
| pH | 6.8 | 6.3 | 8.8 | 6.8 | 6.8 |

TABLE 2

Mobility (%) just after being produced

| | Sample-1 | Sample-2 | Comp.-1 | Comp.-2 | Comp.-3 |
|---|---|---|---|---|---|
| Protein Mol. wt. 94,000 | 23.8 | 22.49 | 23.07 | 26.78 | 24.49 |
| Protein Mol. wt. 43,000 | 50.79 | 50.24 | 50.48 | 53.55 | 48.47 |
| Protein Mol. wt. 20,100 | 91.53 | 94.26 | 92.91 | — | 77.04 |
| Phoretic result | Clear | Clear | Clear | Clear | Clear |

TABLE 3

Mobility (%) after being stored for six months

| | Sample-1 | 1 Sample-2 | Comp.-1 | Comp.-2 | Comp.-3 |
|---|---|---|---|---|---|
| Protein Mol. wt. 94,000 | 26.67 | 28.43 | 17.1 | 25.51 | 24.02 |
| Protein Mol. wt. 43,000 | 52.31 | 55.39 | 42.2 | 54.08 | 47.98 |
| Protein Mol. wt. 20,100 | 94.36 | 96.08 | 88.99 | — | 76.4 |
| Phoretic result | Clear | Clear | Vague | Clear | Clear |

The gel fabricated using the Laemmli's gel buffer solution less in neutralization rate caused by acids in the gel buffer solution was reduced in mobility after being stored for a long period because of a high pH, became worse in resolution. With the gel buffer solution in which Tris is raised in neutralization rate while the ampholyte is composed of only glycine, although few reductions in mobility could be discerned even after long storage, no small molecule range was found. Moreover, the gel buffer solution adjusted to pH 6.8 and added with tricine as a conjugate ampholyte of 8.3 pKb together with glycine made the fractionated molecular weight range much broadening.

In contrast, when the conjugate ampholyte of 9.0 pKb 9.6, or serine was employed together with glycine, the ampholytes migrated consecutively towards the anode side to their respective positions on the basis of the pKb value, with the smallest pKb migrating to the position most neighboring the anode, so that the gentle potential gradient was established in the gel. Thus, even when Tris was raised in neutralization rate while the buffer solution was titrated to either pH 6.8 or pH 6.3, the gel succeeded in realizing the wide range in the fractionated molecular weight of species undergoing measurement, which is comparable to the gels fabricated using the Laemmli's gel buffer solution. Besides, no reduction in mobility was seen even after long storage.

EXAMPLE 2

Ten-percent polyacrylamide gels were produced using the same glass plate cell as in Example 1. The monomer solutions used were prepared, each of which was composed of a 10% acrylamide (%T), a 5% Bis (%C), and any one of buffer solutions composed as shown in Table 4 below. The polyacrylamide gels obtained were stored at 5 for twelve months. The glass plate cells after being stored were subjected to vertical tensile force by the use of a Tensilon Universal testing machine (Orientec Type U-2129) to measure tensile strength, the results of which are shown in Table 5.

TABLE 4

Compositions of gel buffer solutions

|  | Sample-3 | Sample-4 | Comp.-4 |
|---|---|---|---|
| Tris (mol/litre) | 0.082 | 0.08 | 0.09375 |
| Glycine (mol/litre) | 0.167 | 0.162 | 0.192 |
| serine (mol/litre) | 0.025 | 0.03 | — |
| Tricine (mol/litre) | — | — | — |
| pH | 6.3 | 6.8 | 7.5 |

TABLE 5

Tensile strength (kgf) of the glass plate cell

|  | Soon after produced | After 2 months at 5 | After 4 months at 5 | After 6 months at 5 | After 8 months at 5 | After 10 months at 5 | After 12 months at 5 |
|---|---|---|---|---|---|---|---|
| Sample-3 | 1.85 | 1.83 | 1.88 | 1.83 | 1.85 | 1.85 | 1.83 |
| Sample-4 | 1.83 | 1.8 | 1.78 | 1.73 | 0.85 | 0.388 | — |
| Comp.-4 | 1.8 | 0.65 | 0.52 | — | — | — | — |

Lowering pH in the gel buffer solution contributed to keeping not only the mobility of proteins but also the shape of the precast gel stable. As well known, the polyacrylamide gel is in general apt to swell readily due to hydrolysis, so that the precast gel becomes much subject to cracking in the glass plate cell. At pH 7.5, since the gel was liable to be subjected to hydrolysis, the tensile strength causing the crack in the glass plate cell fell to about one third after stored at 5 for two months. Conversely, at pH 6.8, the gel in the glass plate cell maintained as a high tensile strength as just after produced, even after stored at 5 up to six months. When controlled to pH 6.3, the gels obtained were remarkably retarded in the rate of hydrolysis compared with pH 6.8, because pH 6.3 was near to the pH of the acrylamide itself. This made it possible to store the gels for over a year without no change or deterioration in gel shape.

EXAMPLE 3

A rectangular glass sheet of 12 cm in width and 10 cm long and another glass sheet of the same dimension made at an upper end thereof with a recess were assembled with a spacer of 1 mm in thickness interposed between the confronting glass sheets, providing a glass plate cell. Monomer solutions were prepared, each of which was composed of a 10% acrylamide (%T), a 5% Bis (%C), and any one of buffer solutions composed as shown in Table 6 below. The monomer solutions were added and blended with 400 ppm of APS and 400 ppm of tetramethylethylenediamine, contracted to TEMED. The resultant mixture was poured into the glass plate cell where polymerization was allowed in a usual way to yield a polyacrylamide gel for electrophoresis.

A commercially available marker DNA of known molecular weights was subjected to electrophoresis using the polyacrylamide gel obtained as stated earlier. The electrophoresis results were satisfactory in migration distance and clearness of bands. The marker DNA, prior to use for electrophoresis test, was diluted one hundred times with a buffer solution composed of a 10 mmol/litre Tris including 30%(w/v) sucrose and BPB of stainable level, 1 mmol/litre ETA and 20mmol/litre sodium chloride solution, titrated to the pH 7.9 with hydrochloric acid. The electrophoresis buffer solution was composed of 0.0892 mol/litre Tris, 0.0890 mol/litre boric acid and 2.5 mmol/litre ETA. The electrophoresis was performed at a constant voltage of 200 volt, while an upper buffer solution reservoir was filled with the buffer solution colored with BPB. Electric conduction was halted just when the electrophoretic end of BPB had reached the bottom of the gel. Staining was done using silver staining. After completion of electrophoresis, the gel was soaked for 20 minutes in an aqueous solution containing 50%(v/v) methanol, 5%(w/v) trichloroacetic acid, and 3.5 (w/v) sulfosalicylic acid to fix the DNA, then rinsed twice with purified water for 15 minutes. Thereafter the gel was soaked to be stained in a solution in which 8% aqueous sodium carbonate solution and 0.28%(v/v) aqueous formaldehyde solution were mixed in a proportion of 1:1, the 0.28%(v/v) aqueous formaldehyde solution containing 1%(v/v) tungstosilicic acid, 0.02%(w/v) silver nitrate and 0.2%(w/v) ammonium nitrate. After a lapse of 7 minutes during which the gel was stained to visualize the bands of separated molecules, the gel was removed from the dye solution, and immersed in 1%(v/v) acetic acid for 15 minutes to stop the staining. The electrophoresis results proved the DNA bands clearly resolved. Table 7 below shows the mobility defined as the migration distance of a DNA fragment relative to the migration distance of BPB: (Mobility %)=(Distance of each band from the lower end of well) (Distance of the electrophoretic front of BPB from the lower end of well) 100

TABLE 6

Compositions of gel buffer solutions

|  | Sample-5 | Sample-6 | Sample-7 |
|---|---|---|---|
| Tris (mol/litre) | 0.094 | 0.082 | 0.08 |
| Glycine (mol/litre) | 0.192 | 0.167 | 0.167 |
| Serine (mol/litre) | — | 0.025 | 0.025 |
| HCl (mol/litre) | 0.08 | 0.0695 | 0.068 |
| pH | 7.5 | titrated to 6.8 with acetic acid | titrated to 6.3 with acetic acid |

TABLE 7

[ Mobility of DNA fragments in gel just after produced ]

|  | Sample-5 | Sample-6 | Sample-7 |
|---|---|---|---|
| Fragment size 495 bp | 25.91% | 31.82% | 31.79% |
| Fragment size 210 bp | 45.30% | 53.79% | 50.93% |
| Fragment size 162 bp | 53.79% | 63.33% | 59.35% |
| Fragment size 79 bp | 81.06% | 89.39% | 88.32% |
| Electrophoretic pattern | Clear | Clear | Clear |

Moreover, Table 8 is to explain the electrophoresis time for every gel sample.

TABLE 8

[ Electrophoresis time at constant voltage of 200 V ]

| Sample-5 | Sample-6 | Sample-7 |
|---|---|---|
| 49 min. | 52 min. | 50 min. |

As will be understood from Tables 6, 7 and 8, all the DNA fragments, when having undergone electrophoresis on the polyacrylamide gels with the gel solutions titrated to any pH of 6.3 and 6.8, with using TBE, exhibited the electrophoretic patterns clearly resolved. With respect to the mobility and electrophoresis time, there was also no significant difference between any DNA fragments.

COMPARATIVE EXAMPLE 1

With using the same glass plate cell as in Example 3 stated earlier, a polyacrylamide electrophoresis gel was, as with the gels in Example 3, prepared from monomer solution composed of 10% acrylamide(%T), 5% Bis(%C) and a buffer solution having a composition in concentration listed in Table 9. A commercially available marker DNA of known molecular weights was subjected to the electrophoresis using the polyacrylamide gel yielded as stated above. The electrophoresis results were satisfactory in migration distance and clearness of bands. The electrophoresis buffer solution used was the Ornstein and Davis electrophoresis buffer solution composed of 0.025 mol/litre Tris and 0.192 mol/litre glycine. In Table 10, the mobility is shown, which is defined as the ratio of the migration distance of the DNA fragment to the migration distance of the BPB, while Table 11 indicates the electrophoresis time.

TABLE 9

Compositions of gel buffer solutions

|  | Comparative Sample-5 |
|---|---|
| Tris (mol/litre) | 0.08 |
| Glycine (mol/litre) | 0.172 |
| Serine (mol/litre) | 0.03 |

TABLE 9-continued

Compositions of gel buffer solutions

|  | Comparative Sample-5 |
|---|---|
| HCl (mol/litre) | 0.0068 |
| pH | titrated to 6.3 with acetic acid |

TABLE 10

[ Mobility of DNA fragments in gel just after produced ]

|  | Comparative Sample-5 |
|---|---|
| Fragment size 495 bp | Unable to define |
| Fragment size 210 bp | Unable to define |
| Fragment size 162 bp | Unable to define |
| Fragment size 79 bp | Unable to define |
| Electrophoretic pattern | Vague |

TABLE 11

[ Electrophoresis time at constant voltage of 200 V]

| Comparative Sample-5 |
|---|
| 80 min. |

As will be seen in Tables 9, 10 and 11, all the DNA fragments, when having undergone electrophoresis on the polyacrylamide gels with the gel solutions titrated to pH of 6.3, with using the Ornstein and Davis electrophoresis buffer solution, exhibited no electrophoretic pattern clearly resolved, so that the individual DNA bands were unsatisfactorily diffuse.

EXAMPLE 4

With using the same glass plate cell as in Example 3 stated earlier, a polyacrylamide electrophoresis gel was, as with the gels in Example 3, prepared from monomer solution composed of 10% acrylamide(%T), 5% Bis(%C) and a buffer solution having any one of composition in concentration listed below in Table 12.

TABLE 12

[ Compositions of gel buffer solutions ]

|  | Sample-8 | Sample-9 | Sample-10 |
|---|---|---|---|
| Tris (mol/litre) | 0.094 | 0.082 | 0.08 |
| Glycine (mol/litre) | 0.192 | 0.167 | 0.167 |
| Serine (mol/litre) | — | 0.025 | 0.025 |
| HCl (mol/litre) | 0.08 | 0.0695 | 0.068 |

TABLE 12-continued

| [ Compositions of gel buffer solutions ] | | | |
|---|---|---|---|
| | Sample-8 | Sample-9 | Sample-10 |
| pH | 7.5 | titrated to 6.8 with acetic acid | titrated to 6.3 with acetic acid |

The polyacrylamide gels prepared as stated above were stored at 5° C., and used every a preselected lapse of time for the runs in which the DNA fragments were subjected to electrophoresis using the same TBE as described in Example 3. The electrophoresis was run at a constant voltage of 200V per gel. The electrophoresis was allowed till the time 50 minutes had gone by. The migration distance and the sharp pattern of bands were proved. The electrophoresis results are shown below in Tables 13, 14 and 15.

TABLE 13

[ Changes in mobility of DNA fragments in sample-8 after stored at 5° C. for varying periods of time ]

| | Soon after produced | After 2 months | After 4 months | After 6 months |
|---|---|---|---|---|
| Fragment size 495 bp | 30.80% | 26.22% | 17.72% | 18.75% |
| Fragment size 210 bp | 52.85% | 44.44% | 35.04% | 32.03% |
| Fragment size 162 bp | 62.36% | 52.89% | 42.91% | 39.06% |
| Fragment size 79 bp | 90.87% | 79.56% | 70.47% | Unable to define |
| Electrophoretic pattern | Clear | Clear | Clear | Vague |

TABLE 14

[ Changes in mobility of DNA fragments in sample-9 after stored at 5° C. for varying periods of time ]

| | Soon after produced | After 2 months | After 4 months | After 6 months |
|---|---|---|---|---|
| Fragment size 495 bp | 26.20% | 22.91% | 23.25% | 18.50% |
| Fragment size 210 bp | 47.16% | 41.41% | 41.67% | 34.80% |
| Fragment size 162 bp | 55.90% | 49.34% | 50.00% | 42.29% |
| Fragment size 79 bp | 85.59% | 77.97% | 78.51% | 68.72% |
| Electrophoretic pattern | Clear | Clear | Clear | Clear |

TABLE 15

[ Changes in mobility of DNA fragments in sample-10 after stored at 5° C. for varying periods of time ]

| | Soon after produced | After 3 months | After 5 months | After 7 months |
|---|---|---|---|---|
| Fragment size 495 bp | 31.78% | 31.05% | 31.05% | 30.52% |
| Fragment size 210 bp | 50.93% | 50.23% | 50.23% | 50.23% |
| Fragment size 162 bp | 59.35% | 58.45% | 58.45% | 59.15% |
| Fragment size 79 bp | 88.32% | 86.76% | 86.76% | 87.79% |
| Electrophoretic pattern | Clear | Clear | Clear | Clear |

As will be understood from Table 13, the polyacrylamide gel with the gel buffer solution of pH 7.5 was subject to degradation by hydrolysis with the lapse of time even at 5° C., generating anionic groups, which behave in a manner that retards the mobility of DNA. After the lapse of six months, there was no detectable fragment of small molecule. Moreover, the Table 14 explains that the polyacrylamide gel with the gel buffer solution of pH 6.8 lowered much in the rate of hydrolysis, compared with the gel buffer solution of pH 7.5. Nevertheless, much change in the mobility of DNA was seen in the gel after stored at 5° C. up to six months.

In contrast, the polyacrylamide gel with the gel buffer solution of pH 6.3, as shown in Table 15, experienced less changes in either of the mobility of DNA and the electrophoresis pattern even after having been stored at 5° C. for seven months.

EXAMPLE 5

A rectangular glass sheet of 12 cm in width and 10 cm long and another glass sheet of the same dimension made at an upper end thereof with a recess were assembled with a spacer of 1 mm in thickness interposed between the confronting glass sheets to provide a glass plate cell. Monomer solutions were prepared, each of which was composed of a 10% acrylamide (%T), a 5% Bis (%C), and any one of buffer solutions composed as shown in Table 16 below. The monomer solutions were added and blended with 400 ppm of APS and 400 ppm of TEMED. The resultant mixture was poured into the glass plate cell where polymerization was allowed in a usual way to yield a polyacrylamide gel for electrophoresis.

TABLE 16

Compositions of gel buffer solutions

| | Sample-11 | Sample-12 | Sample-13 |
|---|---|---|---|
| Tris (mol/litre) | 0.5 | 0.094 | 0.082 |
| Glycine (mol/litre) | — | 0.192 | 0.167 |
| Serine (mol/litre) | — | — | 0.025 |
| HCl (mol/litre) | # | 0.080 | 0.070 |
| pH | # titrated to 8.8 with HCl | 7.5 | titrated to 6.8 with acetic acid |

A commercially available marker DNA of known molecular weights was subjected to electrophoresis using the polyacrylamide gel obtained as stated earlier. The electrophoresis results were satisfactory in migration distance and clearness of bands. The maker DNA, prior to use for electrophoresis test, was diluted one hundred times with a buffer solution composed of a 10 mmol/litre Tris including 30%(w/v) sucrose and BPB of stainable level, 1 mmol/litre ETA and 20 mmol/litre sodium chloride solution, titrated to the pH 7.9 with hydrochloric acid. The electrophoresis buffer solution used was the Ornstein and Davis electrophoresis buffer solution composed of 0.025 mol/litre Tris and 0.192 mol/litre glycine. The electrophoresis was performed at a constant current of 20 milliamps, while an upper buffer solution reservoir was filled with the buffer solution colored with BPB. Electric conduction was halted just when the electrophoretic end of BPB had reached the bottom of the gel. Staining was done using silver staining. After the completion of electrophoresis, the gel was soaked for 20 minutes in an aqueous solution containing 50%(v/v) methanol, 5%(w/v) trichloroacetic acid, and 3.5(w/v) sulfosalicylic acid to fix the DNA, then rinsed twice with purified water for 15 minutes. Thereafter the gel was soaked to be stained in a solution in which 8% aqueous sodium carbonate solution and 0.28%(v/v) aqueous formaldehyde solution were mixed in a proportion of 1: 1, the 0.28%(v/v) aqueous formaldehyde solution containing 1%(v/v) tungstosilicic acid, 0.02%(w/v) silver nitrate and 0.2%(w/v) ammonium nitrate. After a lapse of 7 minutes during which the gel was stained to visualize the bands of separated molecules, the gel was removed from the dye solution, and immersed in 1%(v/v) acetic acid for 15 minutes to stop the staining. The electrophoresis results proved the DNA bands clearly resolved. Table 17 below shows the mobility defined as the migration distance of a DNA fragment relative to the migration distance of BPB: (Mobility %)=(Distance of each band from the lower end of well) (Distance of the electrophoretic front of BPB from the lower end of well) 100 Moreover, Table 18 is to explain the electrophoresis time for every gel sample.

TABLE 16

Compositions of gel buffer solutions

|  | Sample-11 | Sample-12 | Sample-13 |
|---|---|---|---|
| Tris (mol/litre) | 0.5 | 0.094 | 0.082 |
| Glycine (mol/litre) | — | 0.192 | 0.167 |
| Serine (mol/litre) | — | — | 0.025 |
| HCl (mol/litre) | # | 0.080 | 0.070 |
| pH | # titrated to 8.8 with HCl | 7.5 | titrated to 6.8 with acetic acid |

TABLE 17

[ Mobility of DNA fragments in gel just after produced ]

|  | Gel Sample-11 | Gel Sample-12 | Gel Sample-13 |
|---|---|---|---|
| Fragment size 495 bp | 33.03% | 26.01% | 26.03% |
| Fragment size 210 bp | 45.87% | 45.98% | 47.00% |
| Fragment size 162 bp | 52.29% | 54.19% | 55.46% |

TABLE 17-continued

[ Mobility of DNA fragments in gel just after produced ]

|  | Gel Sample-11 | Gel Sample-12 | Gel Sample-13 |
|---|---|---|---|
| Fragment size 79 bp | 73.39% | 81.55% | 85.09% |
| Electrophoretic pattern | Clear | Clear | Clear |

TABLE 18

[ Electrophoresis time at constant current of 20 milliamps ]

| Gel Sample-11 | Gel Sample-12 | Gel Sample-13 |
|---|---|---|
| 74 min. | 80 min. | 79 min. |

As will be understood from Tables 16, 17 and 18, all the DNA fragments, when having undergone electrophoresis on the polyacrylamide gels with the gel solutions titrated to any pH of 7.5 and 6.8, with using the Ornstein and Davis electrophoresis buffer solution, exhibited the electrophoretic patterns clearly resolved. With respect to the mobility and electrophoresis time of the DNA fragments, there was also no significant difference, compared with the gel using the Ornstein and Davis electrophoresis buffer solution of pH 8.8.

In Tables 19 and 20 below, moreover, there are shown changes in the mobility in the samples-12 and -13 after having stored at 5.

TABLE 19

[ Changes in mobility of DNA fragments in sample-12 after stored at 5° C. for varying periods of time ]

|  | Soon after produced | After 2 months | After 4 months | After 6 months |
|---|---|---|---|---|
| Fragment size 495 bp | 26.01% | 22.48% | 20.01% | 14.69% |
| Fragment size 210 bp | 45.98% | 38.35% | 33.89% | 26.48% |
| Fragment size 162 bp | 54.19% | 45.45% | 41.56% | 34.25% |
| Fragment size 79 bp | 81.55% | 67.12% | 60.57% | Unable to define |
| Electrophoretic pattern | Clear | Clear | Clear | Vague |

TABLE 20

[ Changes in mobility of DNA fragments in sample-13 after stored at 5° C. for varying periods of time ]

|  | Soon after produced | After 2 months | After 4 months | After 6 months |
|---|---|---|---|---|
| Fragment size 495 bp | 26.03% | 22.91% | 20.01% | 17.40% |
| Fragment size 210 bp | 47.00% | 42.56% | 33.89% | 35.02% |

TABLE 20-continued

[ Changes in mobility of DNA fragments in sample-13 after stored at 5° C. for varying periods of time ]

| | Soon after produced | After 2 months | After 4 months | After 6 months |
|---|---|---|---|---|
| Fragment size 162 bp | 55.46% | 49.12% | 41.56% | 43.58% |
| Fragment size 79 bp | 85.09% | 79.80% | 60.57% | 70.48% |
| Electrophoretic pattern | Clear | Clear | Clear | Clear |

COMPARATIVE EXAMPLE 2

With using the same glass plate cell as in Example 5, a polyacrylamide electrophoresis gel was, as with the gels in Example 5, prepared from monomer solution composed of 10% acrylamide(%T), 5% Bis(%C) and any one of buffer solutions having a composition in concentration listed in Table 21. A commercially available marker DNA of known molecular weights was subject to electrophoresis using the polyacrylamide gel yielded as stated above. The electrophoresis results were satisfactory in migration distance and clearness of bands. The electrophoresis buffer solution used was the Ornstein and Davis electrophoresis buffer solution composed of 0.025 mol/litre Tris and 0.192 mol/litre glycine. In Table 22, the mobility is shown, which is defined as the ratio of the migration distance of the DNA fragment to the migration distance of the BPB, while Table 23 indicates the electrophoresis time.

TABLE 21

Compositions of gel butter solutions

| | Comparative Sample-6 | Comparative Sample-7 |
|---|---|---|
| Tris (mol/litre) | 0.5 | 0.5 |
| Glycine (mol/litre) | — | — |
| Serine (mol/litre) | — | — |
| HCl (mol/litre) | # | # |
| pH | titrated to 8.8 with HCl | titrated to 7.5 with HCl |

TABLE 22

[ Mobility of DNA fragments in gel just after having produced ]

| | Comparative Sample-7 | Comparative Sample-7 |
|---|---|---|
| Fragment size 495 bp | 33.03% | 49.32% |
| Fragment size 210 bp | 45.87% | 74.43% |
| Fragment size 162 bp | 52.29% | 85.39% |
| Fragment size 79 bp | 73.39% | — |

TABLE 22-continued

[ Mobility of DNA fragments in gel just after having produced ]

| | Comparative Sample-7 | Comparative Sample-7 |
|---|---|---|
| Electrophoretic pattern | Clear | Clear |

TABLE 23

[ Electrophoresis time at constant current of 20 milliamps ]

| Comparative Sample-6 | Comparative Sample-7 |
|---|---|
| 74 min. | 216 min. |

As will be understood from Tables 21, 22 and 23, when the gel buffer solution contained no glycine in the solution, adjusted to pH 7.5 with Tris and hydrochloric acid, the electrophoresis gel rose in the potential gradient between the tris strong acid salt part and the tris weak acid salt part, so that the species undergoing separation were liable to focus on area neighboring the boundary. This made the fractionated molecular weight range reduced. Besides, the electrophoresis time was made elongated while analytic efficiency became worse.

Table 24 shows changes in mobility in the comparative gel sample-6 after storage at 5° C. for varying periods of time.

TABLE 24

[ Changes in mobility of DNA fragments in comparative sample-6 after stored at 5° C. for varying periods of time ]

| | Soon after produced | After 2 months | After 4 months | After 6 months |
|---|---|---|---|---|
| Fragment size 495 bp | 33.03% | 16.15% | — | — |
| Fragment size 210 bp | 45.87% | 21.58% | — | — |
| Fragment size 162 bp | 52.29% | 32.41% | — | — |
| Fragment size 79 bp | 73.39% | Unable to define | — | — |
| Electrophoretic pattern | Clear | Vague | — | — |

EXAMPLE 6

With using the same glass plate cell as in Example 5 stated earlier, polyacrylamide electrophoresis gels were, as with the gels in Example 5, prepared from monomer solutions composed of 10% acrylamide(%T), 5% Bis(%C) and a buffer solution having any one composition of samples-12 and -13 in concentration listed earlier in Table 16. A commercially available marker DNA of known molecular weights was subjected to electrophoresis using the polyacrylamide gel obtained as stated earlier. The migration distance and the sharp pattern of bands were proved. The electrophoresis buffer solution used was the Laemmli's electrophoresis buffer solution containing 0.025 mol/litre Tris, 0.192 mol/litre glycine and 0.1%(/v) SDS. The electrophoresis was run at a constant current of 20 milliamps per gel. Table 25 shows the mobility representing a ratio of the migration distance of each DAN fragment to the migration distance of the BPB, while Table 26 explains the electrophoresis time per gel.

TABLE 25

[ Mobility of DNA fragments in gel just after having produced ]

|  | Sample-12 | Sample-13 |
|---|---|---|
| Fragment size 495 bp | 25.99% | 26.00% |
| Fragment size 210 bp | 45.93% | 48.89% |
| Fragment size 162 bp | 54.10% | 55.05% |
| Fragment size 79 bp | 81.00% | 84.89% |
| Electrophoretic pattern | Clear | Clear |

TABLE 26

[ Electrophoresis time at constant current of 20 milliamps ]

| Sample-12 | Sample-13 |
|---|---|
| 81 min. | 79 min. | though the electrophoresis buffer solution used is the Laemmli's electrophoresis buffer solution containing SDS, which has been commonly used for protein analysis, the gel prepared according to the present invention may serve well for producing sharp bands of the DNA fragments in analytic separation.

COMPARATIVE EXAMPLE 3

With using the same glass plate cell as in Example 6, a polyacrylamide electrophoresis gel was, as with the gels in Example 6, prepared from a monomer solution composed of 10% acrylamide(%T), 5% Bis(%C) and a buffer solution having a composition in concentration described later in Table 27. A commercially available marker DNA of known molecular weights was subjected to electrophoresis using the polyacrylamide gel obtained as stated above. The migration distance and the sharp pattern of bands were proved. The electrophoresis buffer solution used was Laemmli's electrophoresis buffer solution containing 0.025 mol/litre Tris, 0.192 mol/litre glycine and 0.1%(/v) SDS. Table 28 shows the mobility representing a ratio of the migration distance of each DAN fragment to the migration distance of the BPB, while Table 29 explains the electrophoresis time.

TABLE 27

Composition of gel buffer solution

|  | Comparative Sample-8 |
|---|---|
| Tris (mol/litre) | 0.5 |
| Glycine (mol/litre) | — |
| Serine (mol/litre) | — |
| HCl (mol/litre) | # |
| pH | # titrated to 7.5 with HCl |

TABLE 28

[ Mobility of DNA fragments in gel just after having produced ]

|  | Comparative Sample-8 |
|---|---|
| Fragment size 495 bp | 50.00% |
| Fragment size 210 bp | 75.43% |
| Fragment size 162 bp | 86.28% |
| Fragment size 79 bp | — |
| Electrophoretic pattern | Clear |

TABLE 29

[ Electrophoresis time at constant current of 20 milliamps ]

| Comparative Gel Sample-8 |
|---|
| 210 min. |

As shown in Tables 27, 28 and 29, when the DNA fragments were subjected to electrophoresis using the gel buffer solution containing no glycine in the solution, adjusted to pH 7.5 with Tris and hydrochloric acid, together with the Laemmli's electrophoresis buffer solution, the fractionated molecular weight range was rendered remarkably narrowed just like the run using electrophoresis using the Ornstein and Davis electrophoresis buffer solution. Moreover, the electrophoresis time was made elongated while analytic efficiency became worse.

Industrial Applicability

With the precast acrylamide electrophoresis gel in accordance with the present invention, the gel buffer solution contains both tris(hydroxymethyl) aminomethane and any ampholyte, titrated at a gel pH of from neutral to acidic range. This makes it possible to provide the electrophoresis gel that is retarded in hydrolysis to a significant extent, thereby having increased useful shelf-life.

Thus, the precast acrylamide electrophoresis gel of the present invention can be stored for a prolonged period of time without loss of performance, so that it is possible to mass-produce in advance the precast gels differing diversely in separation characteristic or resolution from one another. The precast polyacrylamide gel of the present invention, when used in combination with the electrophoresis buffer solution applied extensively for the electrophoresis of proteins, serves well for the analytic separation of proteins and DNA and, when used in combination with the electrophoresis buffer solution commonly employed for nucleic acid, achieves the analytic separation of DNA.

Accordingly, the precast acrylamide electrophoresis gels of the present invention make it possible to save remarkably the labor and effort for analytic procedure, ensuring a large industrial applicability.

What is claimed is:

1. A precast polyacrylamide gel containing a buffer adapted for use in gel electrophoresis, wherein an electrophoresis buffer solution comprises an aqueous solution containing a tris(hydroxymethyl) aminomethane and an ampholyte, wherein:

(1) said tris(hydroxymethyl) aminomethane is present in a concentration of between 0.07 mol/litre and 0.2 mol/litre, (2) glycine and at least one conjugate ampholyte are present,
   (a) said conjugate ampholyte has a basic dissociation constant of $8.3<pKb<9.6$,
   (b) said conjugate ampholyte is added ranging in amount from 0.1 to 30 mol % with respect to said glycine, and
   (c) a total concentration of said conjugate ampholyte and said glycine ranges between 0.1 and 0.3 mol/litre; and
(3) the pH of said electrophoresis buffer solution is adjusted to a pH of between 6.0 and 6.8.

2. A precast polyacrylamide electrophoresis gel according to claim 1, wherein said conjugate ampholyte is an amino acid having the same number of anionic and cationic groups in the molecule of ampholyte.

3. A precast polyacrylamide electrophoresis gel according to claim 1, wherein said conjugate ampholyte is at least one selected amino acid from the group consisting of serine, glutamine, tryptophane, methionine and phenylalanine.

4. A method of performing electrophoresis comprising providing the precast polyacrylamide electrophoresis gel and buffer solution of claim 1 and performing electrophoresis on said gel.

5. An electrophoresis system for DNA comprising an electrophoresis buffer solution containing tris(hydroxymethyl) aminomethane and a precast polyacrylamide gel which contains the buffer solution, wherein the electrophoresis buffer solution comprising:
   a. the tris(hydroxymethyl) aminomethane in a concentration of between 0.07 mol/liter and 0.2 mol/liter;
   b. glycine and at least one conjugate ampholyte;
   c. said conjugate ampholyte has a basic dissociation constant of $8.3<pKb<9.6$, and includes an amino acid having the same number of anionic and cationic groups in the molecule;
   d. said conjugate ampholyte is present in an amount of from 0.1 to 30 mol % with respect to the glycine;
   e. the total concentration of said conjugate ampholyte and said glycine ranges from 0.1 to 0.3 mol/liter, and
   f. the pH is adjusted to between 6.0 and 6.8.

6. An electrophoresis system for DNA according to claim 5, wherein said gel buffer solution contains a monobasic acid selected from the group consisting of hydrochloric acid, acetic acid, and mixtures thereof adjusted to a pH of between pH 6.0 and pH 6.8

7. An electrophoresis system for DNA according to claim 5, wherein said electrophoresis buffer solution contains tris(hydroxymethyl) aminomethane and components defined in the following (1) and (2), adjusted to a pH in a pH range 7.8–8.3:
   (1) any one of acetic acid, phosphoric acid and boric acid; and
   (2) a chelating agent of disodium ethylenediaminetetraacetate.

8. An electrophoresis system for DNA according to claim 5, wherein said electrophoresis buffer solution contains boric acid.

9. An electrophoresis system for DNA according to claim 5, wherein said electrophoresis buffer solution contains dodecyl sulfate, in addition to glycine.

10. An electrophoresis system for DNA, comprising an electrophoresis buffer solution containing tris(hydroxymethyl) aminomethane buffer and a precast polyacrylamide gel characterized by the following (1)–(3):
   (1) said tris(hydroxymethyl) aminomethane is present in a concentration of between 0.07 mol/litre and 0.2 mol/litre;
   (2) glycine and at least one conjugate ampholyte are present;
      (a) said conjugate ampholyte has a basic dissociation constant of $8.3<pKb<9.6$, and includes an amino acid having the same number of anionic and cationic groups in a molecule,
      (b) said conjugate ampholyte is added ranging in amount from 0.1 to 30 mol % with respect to said glycine, and
      (c) a total concentration of said conjugate ampholyte and said glycine ranges between 0.1 and 0.3 mol/litre; and
   (3) said electrophoresis electrode solution is adjusted to a pH of between 6.0 and pH 6.8.

* * * * *